(12) United States Patent
Beumer et al.

(10) Patent No.: US 8,885,041 B2
(45) Date of Patent: Nov. 11, 2014

(54) METHOD AND APPARATUS FOR CHECKING THE FLUID IN A PIPET TIP

(75) Inventors: Tom Beumer, Oss (NL); Paul Schevers, Schijndel (NL)

(73) Assignee: Biomerieux B.V., Boxtel (NL)

(*) Notice: Subject to any disclaimer, the term of this patent is extended or adjusted under 35 U.S.C. 154(b) by 910 days.

(21) Appl. No.: 12/989,255

(22) PCT Filed: Apr. 24, 2009

(86) PCT No.: PCT/EP2009/054970
§ 371 (c)(1),
(2), (4) Date: Dec. 22, 2010

(87) PCT Pub. No.: WO2009/130309
PCT Pub. Date: Oct. 29, 2009

(65) Prior Publication Data
US 2011/0115905 A1    May 19, 2011

(30) Foreign Application Priority Data

Apr. 24, 2008 (EP) ..................... 08007914

(51) Int. Cl.
*H04N 7/18* (2006.01)
*G01N 35/10* (2006.01)

(52) U.S. Cl.
CPC .... *G01N 35/1016* (2013.01); *G01N 2035/1025* (2013.01)
USPC ........................................................ 348/135

(58) Field of Classification Search
CPC .................. G01N 2035/1025; G01N 35/1016
USPC ........................................................ 348/135
See application file for complete search history.

(56) References Cited

U.S. PATENT DOCUMENTS

| | | | |
|---|---|---|---|
| 5,463,228 A | 10/1995 | Krause | |
| 5,466,946 A | 11/1995 | Kleinschmitt | |
| 6,235,534 B1 * | 5/2001 | Brookes et al. | 436/164 |
| 6,281,517 B1 | 8/2001 | Burkhardt | |
| 6,579,497 B2 | 6/2003 | Woodward | |
| 6,599,476 B1 | 7/2003 | Watson | |
| 7,160,510 B2 | 1/2007 | Tajima | |

FOREIGN PATENT DOCUMENTS

| | | |
|---|---|---|
| DE | 199 24 259 A1 | 12/2000 |
| EP | 0 953 843 A2 | 11/1999 |

OTHER PUBLICATIONS

International Search Report and Written Opinion corresponding to PCT/EP2009/054970, mailing date, Jun. 29, 2009, 11 pages.
International Preliminary Report on Patentability corresponding to PCT/EP2009/054970, completion date, May 7, 2010, 7 pages.

\* cited by examiner

*Primary Examiner* — Anner Holder
(74) *Attorney, Agent, or Firm* — Myers Bigel Sibley & Sajovec, P.A.

(57) ABSTRACT

Methods for detecting the presence and/or volume and/or identity of liquid in a transparent carrier include directing a light source towards the carrier; recording an image of light refracted by the carrier with a camera; and deriving information regarding the presence and/or volume of the liquid in the carrier from the recorded image of the light refracted by the carrier. Devices for detecting the presence and/or volume and/or identity of liquid in a transparent carrier include a camera directed towards the carrier; a light source directed towards the carrier; and means for recording an image of light from the light source as refracted by the carrier and captured by the camera.

21 Claims, 8 Drawing Sheets

METHOD AND APPARATUS FOR CHECKING THE FLUID IN A PIPET TIP

RELATED APPLICATIONS

The present application is a 35 U.S.C. §371 national phase application of PCT International Application No. PCT/EP2009/054970, filed Apr. 24, 2009, which claims priority from European Patent Application No. 08007914.8, filed Apr. 24, 2008, the disclosures of which are hereby incorporated herein by reference in their entireties. The above PCT International Application was published in the English language and has International Publication No. WO 2009/130309.

FIELD OF THE INVENTION

The present invention relates to a method and apparatus for checking the fluid in a pipet tip.

BACKGROUND

In modern automated pipettors or liquid handlers there are several issues to be addressed to precisely and accurately aspirate and dispense the liquid of interest. Apart from the basic pipetting requirements like the use of precise actuators and adequately designed tips, there are also requirements on the use of in-process controls to monitor the success of the pipetting. For example, the instrument must be able to sense the surface of the liquid that is to be aspirated, to prevent the tip to be inserted too deeply into the fluid and adhere and distribute a significant volume to the outer surface of the tip.

Since the 1980s this is done using capacitative techniques that require a conductive pipetting tip or needle, and typically require a minimum amount of liquid mass available.

A relatively new method for liquid surface detection it to use a pressure based system in which a small airflow is induced whose resistance—and thus pressure—increases if the distance between tip en and liquid surface becomes small enough.

Furthermore, many applications require evidence that liquid was indeed aspirated and dispensed properly. This has lead inter alia to the recording of the pressure profile upon aspiration, by which it can be demonstrated that liquid did indeed flow through the tiny tip orifice when the plungers were moved. This technique also allows recognition of the aspiration of air bubbles or the presence of blocking items like blood clots.

The possibility to detect fluid flowing into the tip is used to provide evidence for the correctness of the aspirated volume, which is a strong prerequisite in volume critical applications like in vitro diagnostics, in which, an incorrect volume of patient material might lead to erroneous clinical interpretation of the test result with severe health consequences and liabilities.

The drawback of all discussed techniques is that they all require a typical minimum liquid volume in the order of 10-20 µl, both for surface detection and for pressure detection. With the ongoing trend to use smaller volumes of samples and chemical reagents, the above techniques have reached the limits of their applicability.

SUMMARY

It is therefore the object of the present invention to provide a novel technique for detecting the presence and/or volume in a carrier, in particular a pipet tip.

This is achieved by the invention by a method for detecting the presence and/or volume and/or identity of liquid in a transparent carrier, comprising:
 a) directing a light source towards the carrier;
 b) having a camera record an image of light refracted by the carrier; and
 c) deriving information regarding the presence and/or volume of the liquid in the carrier from the recorded image of the light refracted by the carrier.

Other detection systems that are based on illumination of the carrier are for example described in U.S. Pat. Nos. 5,463,228, 7,160,510 and 6,579,497.

U.S. Pat. No. 5,463,228 describes an apparatus for automatic exact dosing of small amounts of liquids in capillary measuring tubes. The apparatus comprises fluid phase boundary detection means that work through illumination of the measuring tube and reception of light passing through said measuring tube. Based on differences in the intensity of the received light the position of the fluid phase boundary can be detected.

U.S. Pat. No. 7,160,510 relates to a dispenser operation verification apparatus which is based on the detection of the liquid surface passing a sensor axis and the changes in light intensity caused thereby.

In U.S. Pat. No. 6,579,497 only the interface between air and fluid is observed by an imaging device. The light is detected by a camera but this light is not refracted by the carrier but reaches the camera after being refracted by a prism.

None of these methods are based on recording an image of the refraction pattern of the carrier like in the invention. All detection methods are based on detecting the light falling straight through the carrier and changes in the light intensity.

The method of the invention is in particular useful for cylinder-symmetric carriers, in particular a pipet tips.

In order to have the carrier refract the light from the light source the carrier is preferably positioned with its optical axis under an angle with the camera's optical axis.

It was found according to the invention that using a dark field type of illumination the refraction patterns of the filled and the empty tip are so different that they allow to not only identify the presence of liquid inside the tip, but also to estimate the volume based on the geometry of the fluid compartment. The method of the invention can be used to ascertain that liquid has been aspirated into the tip, how much has been aspirated (by imaging the carrier after aspiration but before dispensing) and whether the correct amount has been dispensed completely (by imaging the carrier after dispensing).

Since refraction is the origin of the imaging technique, the angle under which the illumination occurs is important. According to the invention it is preferred that for water-based solutions the angle between the optical axis of the light source and the camera axis lies between 0 and 90 degrees. For such water based solutions angles between 10 and 25 degrees show a particular good performance. For other, higher refractive index coefficient solutions other angles will prove optimal. For defining the best possible angle for a particular liquid, the angle of the light beam is scanned over all angles between 0 and 90 while imaging the tip.

For the best imaging result the carrier is placed such that the carrier is on or close to the optical axis of the camera and also on or close to the optical axis of the light source.

The information regarding the presence or volume of the liquid in the tip can be derived by comparing the image of the carrier with a reference image for differences in light refraction or by comparing areas within the recorded image for differences in light refraction. For this comparison image analysis techniques can be used. Using the refraction image to derive information about the content of the carrier instead of light falling directly through the carrier is novel.

Information regarding the volume of the liquid can for example be derived by subtracting the image of the carrier from the image of an empty carrier.

If image analysis means are applied it is even possible to identify artifacts like air bubbles inside the fluid (indicating volumetric errors on the liquid compartment) and splashed of fluid in the empty area of the tip (inducing a potential loss of fluid upon dispensing).

In order to see whether the liquid in the carrier has the correct identity it is possible to compare the recorded image with a refraction image of a carrier filled with the same or with a reference liquid. If the wrong liquid is inside the carrier, this will lead to a different refraction pattern, more precisely to a shift in the dimensions of the dark and light areas in that pattern.

In manual pipetting the trained operator uses a visual feed back to make sure that the liquid is transported correctly. In automated pipetting instruments such feed-back means have so far been indirect. When pressure loss is detected it is assumed that there is liquid flow during aspiration or dispensing. In the case of capacity changes it is also assumed that liquid is present based on the presence of a mass at the expected position. The invention, however, mimics the only true evidence for correct pipetting, namely visual proof that the fluid has been picked up in the right volume, without artifacts, and that is has been dispensed concordingly.

Other optical technologies have been described in the prior art but, similar to the pressure based techniques, these are also indirect as they mainly consider the aspiration of fluid using sensors around the tip that enable to detect the passage of the front meniscus and variants thereof.

The present invention solves the disadvantages of the prior art methods by a technique that offers visual proof of liquid presence inside the tip, of the correct volume inside the tip, of the absence of artifacts (droplets, air bubbles) and of liquid having been dispensed.

The invention is suitably based on an image of a complete carrier, such as a pipet tip, instead of only the interface between liquid and air.

As the refraction pattern mainly depends on the refractive index of the fluid that is pipetted, it is even possible to 'recognize' whether the correct fluid has been aspirated/dispensed for example by comparing the image with an image of the correct fluid. This embodiment works when different fluids have different refractive indices. Furthermore, comparison with images of known fluids can be used to determine which fluid is present.

With minimum image analysis techniques the recorded images can be processed into a numerically analysable result regarding liquid presence and/or volume.

In order to obtain information regarding the volume of the liquid the image of the carrier can for instance be subtracted from the image of an empty carrier.

BRIEF DESCRIPTION OF THE DRAWINGS

The present invention will be further illustrated by reference to the drawings which show.

DETAILED DESCRIPTION OF EMBODIMENTS OF THE INVENTION

Figure 1:
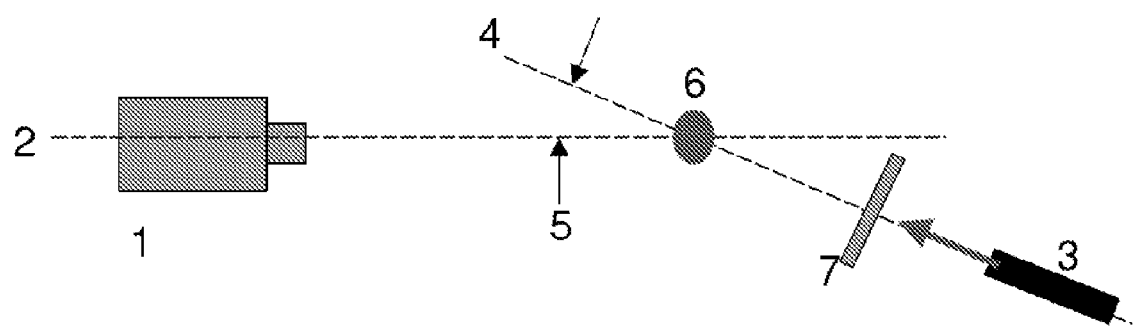
FIG. 1: Schematical presentation of a device for of pipet tip imaging according to the invention.

The optical layout of the pipet tip imaging is shown in FIG. 1. A camera 1 is focussed on the tip 6, the tip is on or close to the optical axis 2 of the camera. A collimated light source 3, for example light from a tungsten lamp that is fiber guided towards the test bed, is directed towards the same tip, with its optical axis 4 under and angle 5 with the camera's axis 2.

A diffuser 7 can be placed between tip 6 and light source 3 if the light intensity distribution needs homogenization (not shown).

Figure 2:
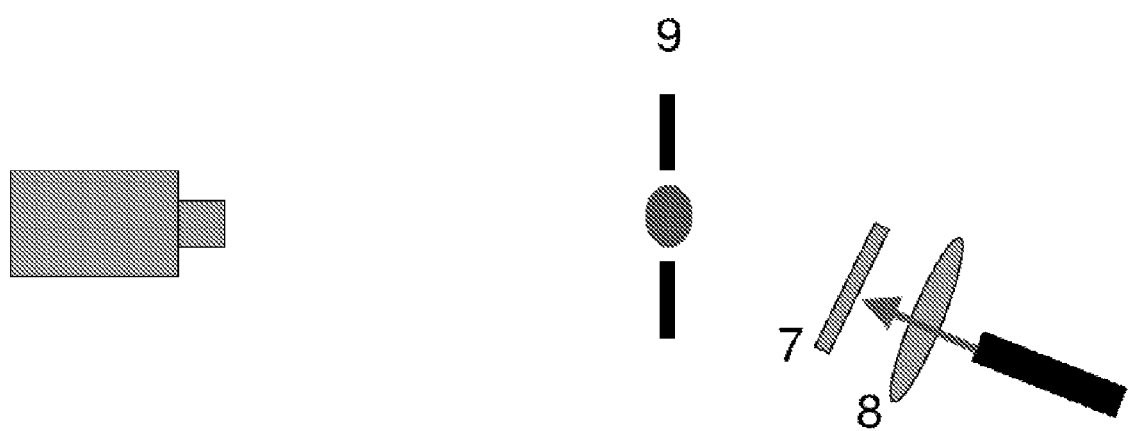
FIG. 2: Schematical presentation of a further embodiment of the device of FIG. 1 with beam stop and diverging lens for focused light source
Figure 3:
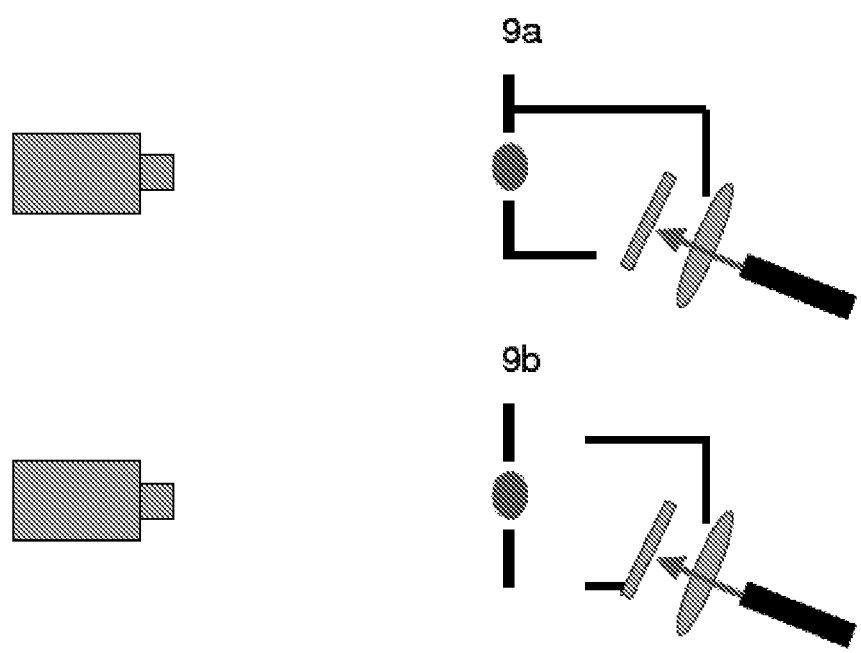
FIG. 3: Schematical presentation of an alternative embodiment of the device of FIG. 2.

In FIG. 2 it is shown that if the exit angle of the light source 3 is too small, or if the exit point of the light source is too close to the tip 6, an additional diverging lens 8 can be mounted before or after the diffuser 7. An important feature to reduce the background illumination of the image and thereby improve the quality of the images is the use of a beam stop 9 which prevents light from the light source 3 to reach the camera's lens 1 directly. A further improvement is shown in FIG. 3 where the beam stop is provided in a box-type and blackened enclosure to further reduce the effect of ambient light on the image sensor. This allows to also operate the optical bench in a non-darkened environment like an existing liquid handler.

Figure 4:
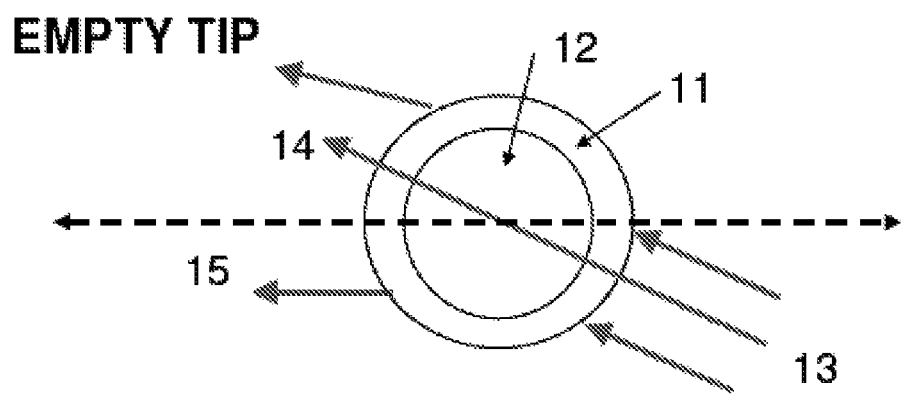
FIG. 4: Schematic representation of the refraction of light in empty and filled pipet tip.
Figure 4:
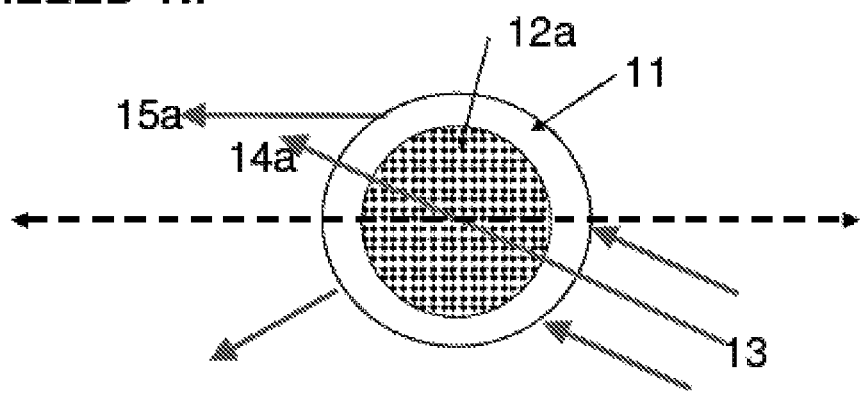

FIG. 4 shows a schematical impression of the physical functionality of the invention. Light from the light source 13 illuminates the tip with polymer wall 11 and either air 12 or liquid 12a inside. Due to the differences in refractive index of air, polymer and fluid, and due to the shape of the pipet tip, light rays are refracted and leave the tip either in the same direction as the incoming rays (14, 14a) or in a different direction. If the tip is not in place, the beam stop prevents any light reaching the detector. If the tip is however in place, some rays (15, 15a) leave the tip in a direction parallel to or on the camera's optical axis. These rays cause the camera to see a 'light zone' on its sensor.

Figure 5:
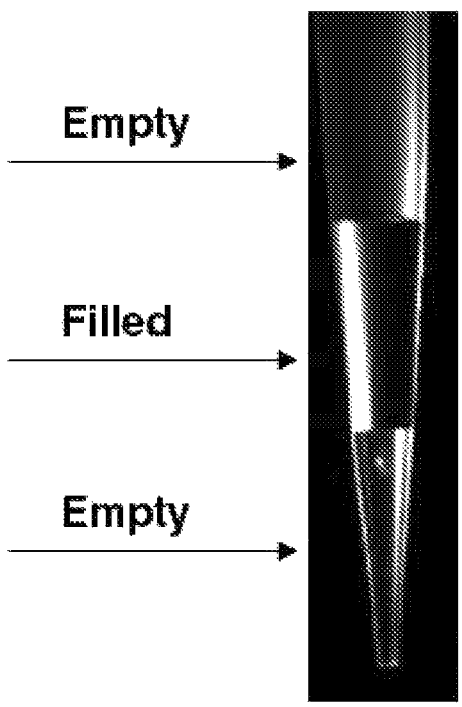
FIG. 5: Contrast enhanced image of a partially water-filled pipet tip demonstrating the different areas where refraction causes light to pass through the tip and reach the camera's sensor.

Because these light paths differ for empty and liquid filled tips, in the images taken from these tips different parts of the tip show up as either dark or light. An example of this difference is shown in FIG. 5.

Figure 9:
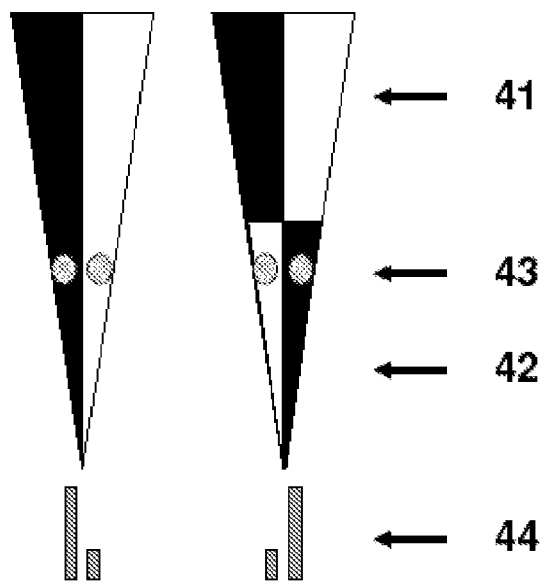
FIG. 9: Schematical diagram of the use of a simplified version of the imaging method using single sensors (42) whose illumination and corresponding output signals (44) depend on the filling of the imaged part of tip (empty pattern: 41, full pattern 42)

The above described embodiments can be used to detect the presence of liquid and its volume inside a transparent pipet tip. In alternative embodiments it may be that the volume information is not critical and liquid presence information could be enough. In such embodiment, the imaging device can be replaced by low cost point source light detectors to detect the change of light to dark and vice versa of the areas in the tip. This principle is shown in FIG. 9. It is thus also possible to not make a full image but rather to image parts of the tip to single-pixel detectors, which give a high current output if illuminated and a low current if the image is dark.

Figure 10:
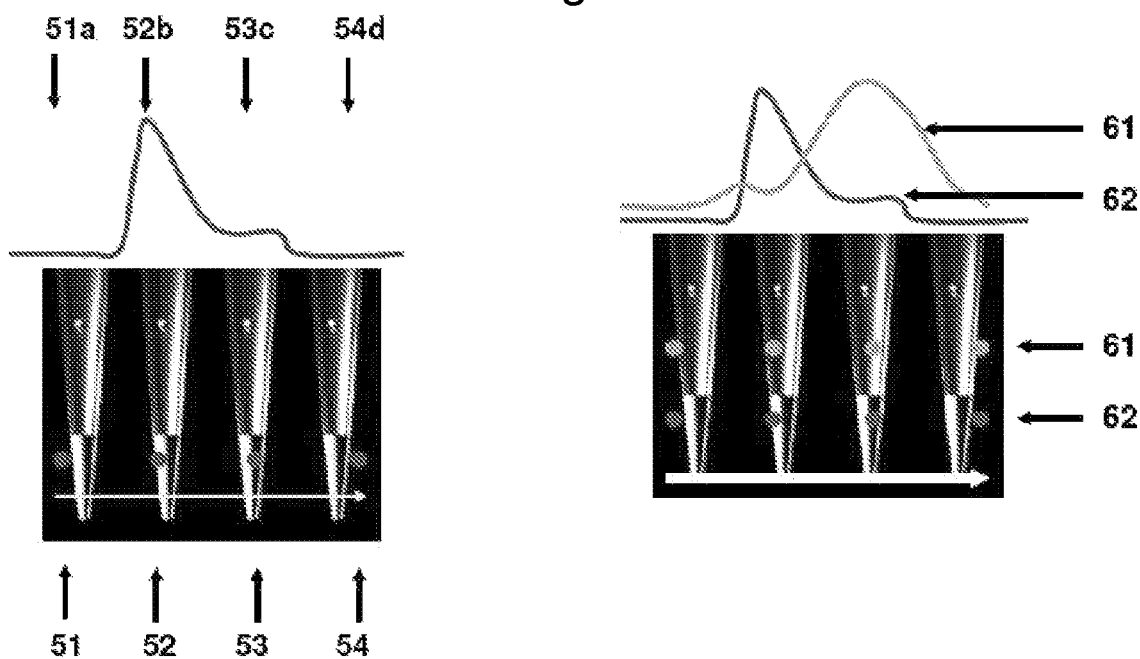
FIG. 10: Schematical diagram of the use of single sensors used to image either the area expected to remain empty (61) and the area expected to be filled (51, 52, 53, 54 and 62). The output current to time transients reflect light and dark areas onto which appropriate analysis software can be applied for pattern recognition and classification of the filling of the tip.

Another option would be to use a single set of detectors and image one tip—or a series of tips—while moving along the sensors (FIG. 10). If these sensors are placed on positions where liquid is expected to be or expected not to be, the signal changes over time (graphs in FIG. 10) or the ratios between these signal changes may provide the required information.

Figure 11:
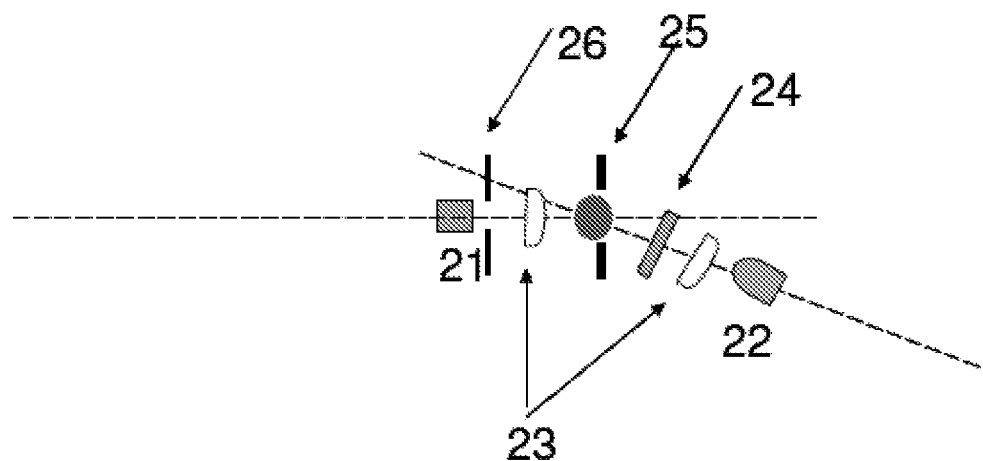
FIG. 11: Miniaturization options using web cam and LED illumination.
Figure 11:
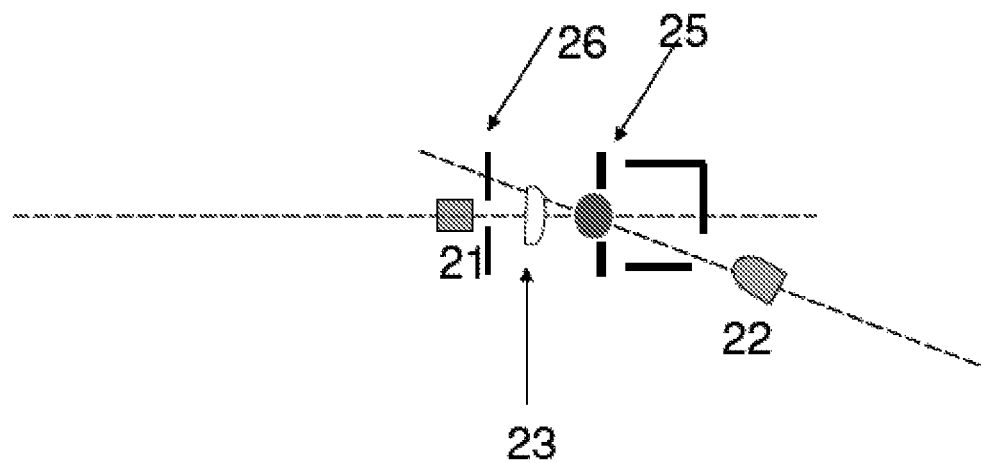

In a preferred embodiment, the geometry of the sampling device is as shown in FIG. 11. For use in an automated platform with often multiple tips, the device is small to enable positioning of the optical device on or close to the pipetting tips. The fundamentals of the set-up as depicted in FIGS. 1-3 remain valid, namely a preferably diffuse light source, an image detector, the angle between the optical axes of these two, and optionally the background light reduction measures (9, 9a, 9b). Size reduction can be achieved using readily available and low cost components like a web cam 21 for detection and a wide angle LED 22 for illumination and smaller size lenses 23, diffuser 24 and beam stops 25, 26. If the LED's opening angle is wide enough one might even consider leaving out the lens and the diffuser, since the quality of the light beam is not critical as long as the entire liquid containing area is illuminated at detectable levels. According to the invention it was found that the spatial illumination light intensity distribution of the imaging is not very critical as long as the difference between dark and light areas exists at all light levels and at all positions that the detector can discriminate. If the intensity distribution is homogeneous enough, captured images can thus be processed with relatively simple image analysis operators. It was furthermore found that the absorbance of the carrier is not critical. It may change to a different pattern of light and dark zones of the imaged tip when highly absorbing fluid is included, but the power to discriminate presence of liquid and its geometry is maintained.

Since the concept of the invention is based on refraction—and thus in the fluid's refractive index—the exact distribution of these patterns will change with refractive index changes of the fluid, e.g. from water to oil or from reagent 1 to reagent 2. However, since the imaging is based on relative refraction within one pipet tip these differences will not influence the method when it is used to analyze the presence and/or volume of a fluid. The change of the patterns with refractive index might however enable the 'fingerprinting' of the fluid and allow recognition of the incorrect fluids if different fluid have different refractive indices and/or absorption coefficient.

Another feature of the refraction based system of the invention is the ability to detect not only if the pipet tip is filled but also if this was achieved homogeneously. Either air bubbles in the liquid compartment or residual droplets of fluid staying behind after dispensing can be recognized from the images. These are preferred features that could further enhance the applicability of this relatively simple optical detection into a full in-process control testing for pipetting of liquids.

EXAMPLES

Example 1

Determination of the Optimal Angle between Light Beam and Camera Axis

Figure 6:
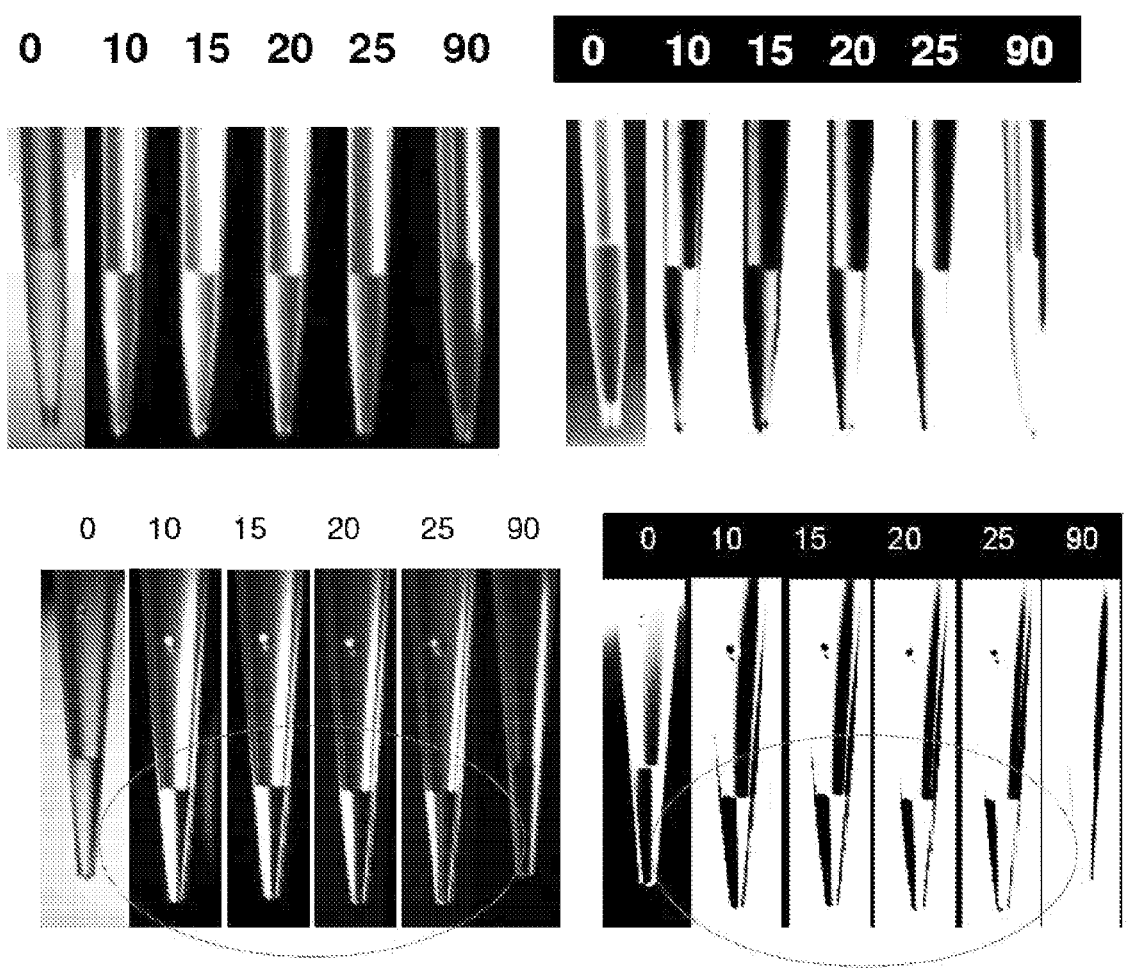
FIG. 6: Effect of angel between optical axes on contrast. The top row shows Eppendorf® 10 µl tips, the bottom row Hamilton® 300 µl tips.

The effect of the angle between the optical axes of the camera and the light beam on the contrast in the image was determined by varying the angle from 0 to 90°. FIG. 6 shows the results. The top row shows 10 μl Eppendorf® tips. The bottom row shows Hamilton® 300 μl tips. The dark and light patterns change with the angle between the optical axes of the illumination and the camera. In the set-up used, the images that were easiest to interpret were obtained at angles between 10 and 25 degrees. A similar experiment can be performed to determine the optimal angle in other setups.

Example 2

Deriving Volume Related Information from Images

Figure 7:
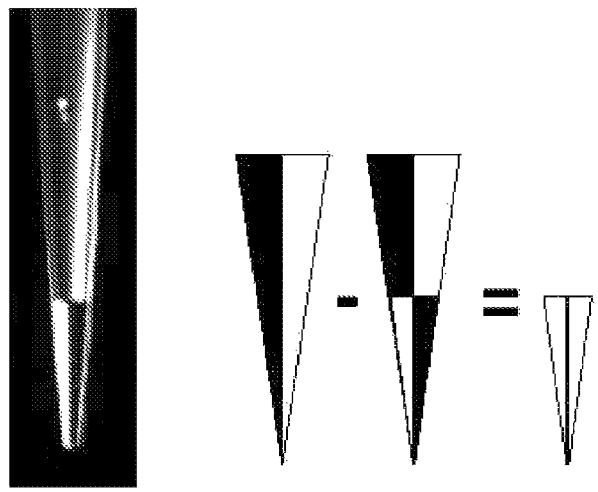
FIG. 7: Principle of subtraction of images of full and empty tip.
Figure 8:
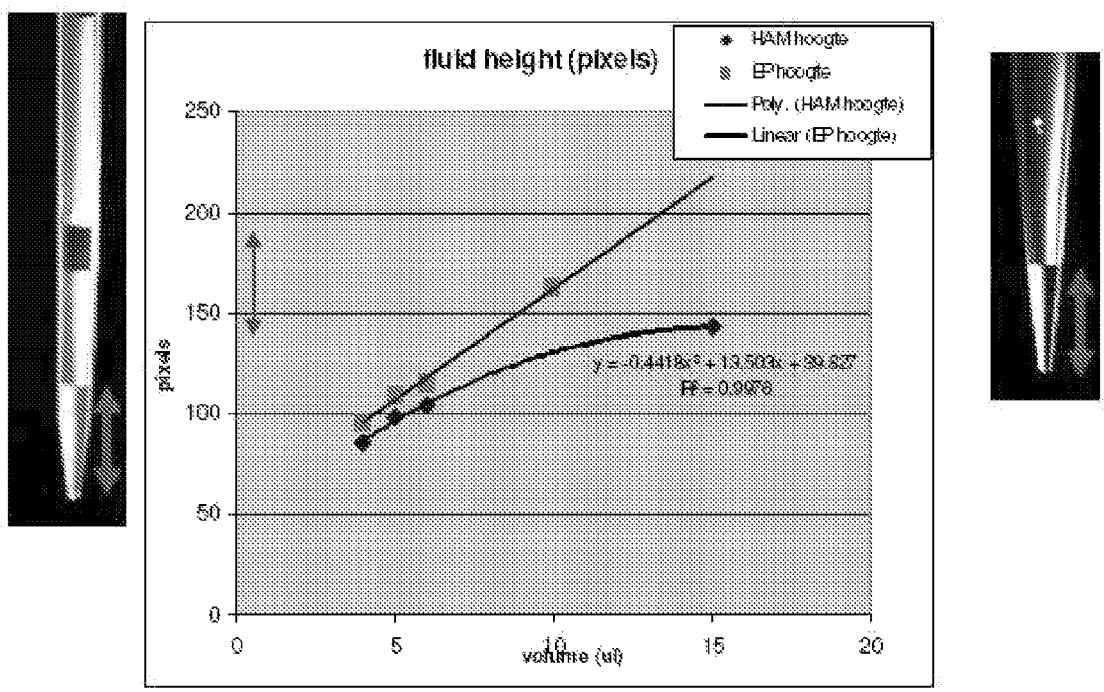
FIG. 8: The relationship between fluid height or volume and number of pixels as derived from images of the invention.

To prove that the images of the carrier are truly volumetric, an image analysis technique was applied to subtract the image of the filled tip from an empty tip and a partly filled tip. As schematically shown in FIG. 7 such a subtraction allows to enhance the perception of the filled area and then estimate the height of the filled part that could be shown to be proportional to the aspirated volume (data shown in FIG. 8 for two tip brands, namely a 20 μl Eppendorf® tip and a 300 μl Hamilton® Starlet tip). For both tested situations the vertical number of pixels in the liquid filled area of the graph increases with increasing liquid volume.

The invention claimed is:

1. A method for detecting the presence of a liquid in a transparent carrier, the method comprising:
    a) directing a light source towards the carrier;
    b) recording an image using light that was refracted when passing through the carrier with a camera;
    c) comparing the recorded image of the carrier with a previously recorded reference image for identifying differences in light refraction, said recorded image and said reference image each comprising a pattern of dark and light zones, said reference image corresponding to a completely filled or empty carrier; and
    d) determining that a liquid is present in said carrier if the comparison indicates a difference in patterns above and below a liquid-air interface associated with a liquid in the carrier.

2. A method as claimed in claim 1, wherein the carrier is a cylinder-symmetric pipet tip.

3. A method as claimed in claim 1, wherein the light source is positioned under an optical axis of the camera and directed towards the carrier to define an angle between an optical axis of the light source and the optical axis of the camera.

4. A method as claimed in claim 1, wherein the light source provides diffuse light.

5. A method as claimed in claim 1, wherein the carrier is placed such that the carrier is on or close to an optical axis of the camera.

6. A method as claimed in claim 3, wherein the angle between the optical axis of the light source and the optical axis of the camera lies between 10 and 25 degrees.

7. A method as claimed in claim 1, wherein information regarding the presence and/or volume of the liquid is derived by subtracting the recorded image of the carrier from an image of an empty carrier as the reference image.

8. A method as claimed in claim 1, wherein information regarding an identity of the liquid is derived using an image of the carrier containing a known liquid as the reference image.

9. A method for detecting the presence of a liquid in a transparent carrier, said carrier being elongated in a first direction, the method comprising:
   a) directing a light source towards the carrier;
   b) having a camera record an image using light that was refracted when passing through the carrier;
   c) comparing the recorded image with a previously recorded reference image for identifying differences in light refraction, said reference image and said recorded image each comprising a pattern of dark and light zones, wherein the pattern extends perpendicular to the first direction, said reference image corresponding to a completely filled or empty carrier; and
   d) determining that a liquid is present in said carrier if the comparison indicates a difference in patterns above and below a liquid-air interface associated with a liquid in the carrier.

10. A method as claimed in claim 9, wherein the carrier is a cylinder-symmetric pipet tip.

11. A device for detecting the presence of a liquid in a transparent carrier, the device comprising:
   a) a light source directed towards the carrier;
   b) a camera directed towards the carrier for recording an image using light that was refracted when passing through the carrier;
   c) means for comparing the recorded image of the carrier with a previously recorded reference image for identifying differences in light refraction, said reference image and said recorded image each comprising a pattern of dark and light zones, said reference image corresponding to a completely filled or empty carrier; and
   d) means for determining that a liquid is present in said carrier if the comparison indicates a difference in patterns above and below a liquid-air interface associated with a liquid in the carrier.

12. A device as claimed in claim 11, wherein the light source is positioned under an optical axis of the camera such that an angle is defined between an optical axis of the light source and the optical axis of the camera.

13. A device as claimed in claim 12, wherein the angle between the optical axis of the light source and the optical axis of the camera lies between 10 and 25 degrees.

14. A device as claimed in claim 11, further comprising a diffuser that is placed in a light beam of the light source for homogenizing a light intensity distribution of the light source.

15. A device as claimed in claim 11, further comprising a beam stop positioned around the carrier.

16. A method as claimed in claim 8, wherein the liquid in the carrier is determined to be different than said known liquid if the comparison indicates a shift in the dimensions of the dark and light zones.

17. A method as claimed in claim 1, wherein the geometry of said carrier is known, and wherein the volume of the liquid in the carrier is determined using a position of the liquid-air interface and said known geometry.

18. A device as claimed in claim 11, wherein the determining means are configured to determine information regarding the presence and/or volume of the liquid by subtracting the recorded image of the carrier from an image of an empty carrier as the reference image.

19. A device as claimed in claim 11, wherein the determining means are configured to determine the volume of the liquid in the carrier using a position of the liquid-air interface and a known geometry of the carrier.

20. A device as claimed in claim 11, wherein the determining means are configured to determine information regarding an identity of the liquid using an image of the carrier containing a known liquid as the reference image.

21. A device as claimed in claim 20, wherein the determining means are configured to determine that the liquid in the carrier is different than said known liquid if the comparison indicates a shift in the dimensions of the dark and light zones.

* * * * *